United States Patent

Cole-Hamilton et al.

Patent Number: 5,166,428
Date of Patent: Nov. 24, 1992

[54] METHOD FOR PREPARATION OF ORGANO-TELLURIUM AND SELENIUM COMPOUNDS

[75] Inventors: David Cole-Hamilton, Fife; Alasdair E. D. McQueen, Edinburgh, both of Scotland; John B. Mullin, Worcestershire, England

[73] Assignee: The Secretary of State for Defence in Her Britannic Majesty's Government of the United Kingdom of Great Britain and Northern Ireland, London, Great Britain

[21] Appl. No.: 836,588

[22] Filed: Feb. 18, 1992

Related U.S. Application Data

[63] Continuation of Ser. No. 894, Jun. 8, 1990.

[51] Int. Cl.$^5$ .................. C07C 395/00; C07C 391/00
[52] U.S. Cl. .................................................. 562/899
[58] Field of Search ......................................... 562/899

[56] References Cited

U.S. PATENT DOCUMENTS 4,946,994  8/1990  Higa ................................. 562/899
5,091,570  2/1992  Mullin et al. ..................... 562/899

OTHER PUBLICATIONS

WO 90/15796, International Application, Dec. 27, 1990.
Paul et al., "Indian J. of Chem.", 14A, Nov. 1976, pp. 864–865.

Primary Examiner—Paul F. Shaver
Attorney, Agent, or Firm—Nixon & Vanderhye

[57] ABSTRACT

Methods for the preparation of a tellurium or selenium compound of formula Ra M Rb wherein M is tellurium or selenium and Ra and Rb are different $C_{1-20}$ alkyl, alkenyl or aryl groups are provided in which a compound of formula $(Ra)_2M_2$ is reacted with a compound of formula $(Rb)_2M$ in each compound M being the same. Compounds of formula RaMMRb may also be isolated as an intermediate. Ra M Rb compounds are useful as precursors for metal organic vapor phase epitaxy processes.

17 Claims, No Drawings

METHOD FOR PREPARATION OF ORGANO-TELLURIUM AND SELENIUM COMPOUNDS

This is a continuation of patent application No. PCT/GB 90/80894, filed Jun. 8, 1990

This invention relates to a method for the preparation of organo-tellurium and selenium compounds in which the tellurium or selenium is combined with two different organic groups. In particular the invention relates to a method for preparation of dialkyls and diaryls in which the tellurium or selenium is combined with two different alkyl or aryl groups, termed herein unsymmetrical dialkyls or diaryls.

The Group 16 metals Tellurium and Selenium are important in semi-conductor technology for example in the preparation of the infra red detector material cadmium mercury telluride (CMT) and for use in light sensing switches respectively. Frequently these metals or in particular their compounds such as CMT are deposited on substrates by the process of Metal-Organic Vapour Phase Epitaxy (MOVPE) which involves vapour phase decomposition of a volatile organic compound of the metal, most usually a dialkyl. Dialkyls have the advantages that as well as being volatile they can be easily purified by formation of adducts which can be easily decomposed to form the pure dialkyl. For example GB-A-850955 describes purification by formation of adducts with Group 15 compounds, and PCT/GB88/01062 describes purification by formation of adducts with Group 11 or 12 metal compounds.

Unsymmetrical dialkyls of tellurium and selenium are believed to be advantageous for MOVPE because they have the potential for combining high volatility with low temperatures for deposition of the desired material. These properties have tended to be incompatible in dialkyls where the two alkyl groups are the same (ie "symmetrical dialkyls").

Although many methods of preparation of symmetrical dialkyls of tellurium and selenium are known (eg U.S. Pat. No. 1578731; Synthetic Communications 12(3), 163-165, (1982); J Organomettalic Chemistry 255, 61-70, (1983); GB-A-850955; SU-A-371216; PCT/GB08/01065 (not yet published) little has been done to develop convenient methods of preparation of the unsymmetrical dialkyls.

Exchange reactions of the type:

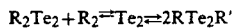

are known, but neither of these is a useful synthetic pathway as the most volatile component of the mixture is a symmetrical compound which will distil preferentially on attempting to separate the components by fractional distillation.

Organometallics 2, 305-307, (1983) describes a method for preparation of unsymmetrical dialkyl tellurides and phenyl-alkyl tellurides and selenides by the reaction of ditellurides or diphenyl diselenide with a Grignard Reagent or an alkali metal alkyl in an ether solvent. A titration-type procedure is used, and clearly this introduces inconvenience. Furthermore Grignard Reagents and alkali metal alkyls are known to be quite sensitive to atmospheric hydrolysis, with the consequent risk of contamination. Grignard Reagents, such as ethyl magnesium bromide also introduce the possibility of contamination of the product by halogens, which can be very deleterious in semiconductor materials.

There is therefore a need for an improved method for preparation of unsymmetrical dialkyls and/or diaryls.

The method of this invention provides a method for the preparation of a tellurium or selenium compound of formula Ra M Rb wherein M is tellurium or selenium and Ra and Rb are different $C_1$-20 alkyl, alkenyl or aryl groups, in which a compound of formula $(Ra)_2 M_2$ is reacted with a compound of formula $(Rb)_2M$, in each compound M being the same, followed by isolation of the product Ra M Rb.

It is believed that (in the case of tellurium dialkyls at least) an intermediate ditelluride or diselenide Ra MM Rb is initially formed together with Ra M Rb, and this intermediate then decomposes on heating to form Ra M Rb and the metal M, i.e.:

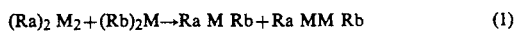

The overall reaction therefore being:
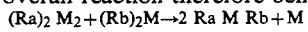

It is therefore preferred to carry out the method of the invention in two stages, firstly to allow the $(Ra)_2 M_2$ and $(Rb)_2 M$ to react at a lower temperature, especially at around room temperature (15°-30° C.), and then in a second stage to heat the reaction mixture to a higher temperature at which the intermediate decomposes.

In an unsymmetrical product Ra M Rb, clearly one of Ra or Rb may have a higher molecular weight than the other. It is known that generally the higher the molecular weight of the alkyl, alkenyl or aryl group in a tellurium or selenium alkyl, alkenyl or aryl, the lower is the volatility of the compound, and furthermore that ditellurides or diselenides are generally less volatile than the corresponding compound containing one tellurium or selenium atom.

Therefore in the method of the invention it is preferred that if possible the combinations of starting materials $(Ra)_2M_2$ and $(Rb)_2M$ are chosen that the boiling point of the product Ra M Rb is lower than that of both starting material, so that the equilibrium of the reaction is encouraged toward Ra M Rb formation. It is also preferred that if Ra and Rb have different molecular weights, then Ra should have the lower so that the effect of the lighter Ra in increasing volatility is to some extent compensated by its being present in the ditelluride or diselenide.

Preferably approximately stoichiometric quantities of the two reactants are used. It is also preferred that the first, lower temperature stage is performed in the dark. No solvent or diluent appears to be necessary for either step of the reaction, but in some cases (eg to encourage mixing of the reactants) conventional solvents such as ethers or alkanes may be used. It is preferred to carry out both stages of the reaction under an inert atmosphere such as nitrogen or in vacuo.

Advantageously after the first stage, solvents, volatile impurities and/or side products (if present) may be removed under reduced pressure, and then heat applied in the second, higher temperature, stage both to decompose the intermediate and to distil off the Ra M Rb product from the metal M.

The Ra M Rb product may then be further purified by conventional methods such as fractional distillation or via adduct formation as mentioned above. For example when Ra and Rb are both alkyl, traces of the symmetrical dialkyls may be formed, which can be easily removed by fractional distillation.

The method of the invention may of course be used as an improved method of preparation of an unsymmetrical ditelluride or diselenide of formula Ra MM Rb. To do this the above method of the invention is performed at a temperature at which decomposition of RaMMRb does not occur or occurs slowly enough for the RaMMRb product to be isolated, for example at about room temperature, followed by isolation of the product RaMMRb. The RaMMRb product may for example be isolated by removal of any RaMRb by fractional distillation. Although RaMMRb is likely to suffer from the disadvantage of being less volatile than RaMRb it may nevertheless find uses such as in MO$_{VPE}$ in certain applications.

The method of the invention is applicable to the preparation of compounds in which Ra and Rb can be independently straight or branched alkyl or tertiary alkyl or alkenyl, or aryl hydrocarbon groups such as phenyl, alkyl- or alkenyl- substituted phenyl, or phenyl- substituted alkyl or alkenyl groups. Preferred alkyl and alkenyl groups have short chains eg 5 or less carbon atoms, especially methyl, ethyl, n- or iso-propyl, n-, iso- or tert-butyl, and allyl.

Preferred RaRb combinations in RaMRb are those which result in highly volatile compounds which an easily be decomposed in MOVPE systems. Preferred combinations are Ra and Rb both alkyl, eg Ra being methyl and Rb being butyl, or one of Ra or Rb being alkyl and the other being alkenyl, eg Ra being methyl and Rb being allyl. The method of the invention appears to be suitable for the preparation of all RaRb combinations.

It appears that the unsymmetrical dialkyls produced by the method of this invention may combine low temperature decomposition with volatility to allow tellurium containing semiconductors to be grown at relatively low temperatures with higher growth rates. Diallyltelluride has an estimated vapour pressure of only 3 Torr at 450° C. and although it decomposes at a lower temperature than allylmethyltelluride the growth rate of CdTe between 240°–260° C. has been reported as 0.6–2.0 μ/hr. Dimethyltelluride has a higher vapour pressure, 52 Torr at 25° C. but temperatures of ca 500° C. are required for growth of CdTe. By comparison, allylmethyltelluride combines a high vapour pressure of 25 Torr at 45° C. with a good growth rate, 30 μ/hr at 290° C.

Examples illustrating this invention will now be described.

EXAMPLE 1

Preparation of methyltert-butyltellurium from dimethylditelluride and di-tert- butyltellurium Dimethylditelluride (38.1 g) and di-tert-butyltellurium (29.9 g) were mixed in a flask and stirred under nitrogen at ambient temperature for one week. During this time the flask was kept in the dark. The volatile products of the reaction were removed by distillation under reduced pressure giving an orange oil. Distillation of this oil under an atmospheric of nitrogen gave methyltert-butyltellurium as a yellow liquid which boils at 119°–122° C. Overall yield=59%. The identity of the product was confirmed by $^1$H and $^{125}$Te NMR Spectroscopy. Traces of t-Bu$_2$ Te were removed by fractional distillation.

EXAMPLE 2

Preparation of allylmethyltellurium from dimethylditelluride and diallyltellurium.

Diallyltellurium (15.98 g, 0.076 mol) and dimethylditelluride (25.04 g, 0.088 mol) were mixed in a flask under vacuum and left in the dark for 16 hours at room temperature. The volatile products were removed by warming the reaction mixture to 50° C. and distilling at reduced pressure to give 25.63 g of an orange liquid. A second distillation at reduced pressure removed any excess dimethylditelluride giving 22.15 g (0.121 mol) of allylmethyltellurium as a yellow-orange liquid, an overall yield of 79.4%. The identity of the product was confirmed by $^1$H and $^{125}$Te NMR spectroscopy.

EXAMPLE 3

Preparation of methylisopropyltellurium from dimethyltelluride and di-isopropyltellurium.

Dimethyltelluride (5.1 g, 0.018 mol) and di-isopropyltellurium (3.8 g, 0.018 mol) were mixed and kept at room temperature for several days. Removal of the volatile fraction at reduced pressure with heating gave 4.9 g of a yellow oil. Analysis of this sample by $^{125}$Te and $^1$H nmr spectroscopy showed it to be MeTei-Pr contaminated with ca. 20% of i-Pr$_2$Te.

EXAMPLE 4

Following the procedure of examples 1, 2 and 3 above isopropylisobutyl tellurium, methylethyltellurium, methylisopropyltellurium, and isopropylisobutyltellurium were also prepared.

We claim:

1. A method for the preparation of a tellurium or selenium compound of formula RaMRb characterised in that M is tellurium or selenium and Ra and Rb are different C$_1$-C$_{20}$ alkyl, alkenyl or aryl groups, wherein a compound (Ra)$_2$M$_2$ is reacted with a compound of formula (Rb)$_2$M, in each compound M being the same, followed by isolation of the product RaMRb.

2. A method according to claim 1 wherein both Ra and Rb are alkyl groups.

3. A method according to claim 1 wherein one of Ra and Rb is alkyl and the other is alkenyl.

4. A method according to claim 1, 2 or 3 wherein Ra has a lower molecular weight than Rb.

5. A method according to claim 2, 3 or 4 wherein Ra and Rb contain 5 or less carbon atoms.

6. A method according to claim 5 wherein Ra is methyl and Rb is tert-butyl.

7. A method according to claim 5 wherein Ra is methyl and Rb is allyl.

8. A method according to claim 5 wherein Ra is methyl and Rb is iso propyl.

9. A method according to claim 5 wherein Ra is isopropyl and Rb is isobutyl.

10. A method according to any one of claims 1 to 9 wherein the method is carried out in two steps, being a first lower temperature step followed by a second higher temperature step.

11. A method according to any one of claims 1 to 10 wherein M is tellurium.

12. A method for the preparation of a tellurium or selenium compound of formula RaMMRb wherein M is tellurium or selenium and Ra and Rb are different $C_1$-$C_{20}$ alkyl, alkenyl or aryl groups, wherein a compound $(Ra)_2M_2$ is reacted with a compound $(Rb)_2M$, in each compound M being the same, followed by isolation of the product RaMMRb.

13. A method according to claim 12 wherein both Ra and Rb are alkyl groups.

14. A method according to claim 13 wherein Ra is methyl and Rb is butyl.

15. A method according to claim 13 wherein one of Ra and Rb is alkyl and the other is alkenyl.

16. A method according to claim 15 wherein Ra is methyl and Rb is allyl.

17. A method according to any one of claims 12 to 16 wherein M is tellurium.

* * * * *